United States Patent
Ruse et al.

(10) Patent No.: US 11,484,718 B2
(45) Date of Patent: Nov. 1, 2022

(54) MULTIMODE ICD SYSTEM COMPRISING PHASED ARRAY AMPLIFIERS TO TREAT AND MANAGE CRT, CHF, AND PVC DISORDERS USING VENTRICLE LEVEL-SHIFTING THERAPY TO MINIMIZE VT/VF AND SCA

(71) Applicant: RUSE TECHNOLOGIES, LLC, Sandy Springs, GA (US)

(72) Inventors: Richard B. Ruse, Sandy Springs, GA (US); Charles Swerdlow, Los Angeles, CA (US); Mark W. Kroll, Crystal Bay, MN (US); Scott Bohanan, Statesboro, GA (US)

(73) Assignee: RUSE TECHNOLOGIES, LLC, Sandy Springs, GA (US)

( * ) Notice: Subject to any disclaimer, the term of this patent is extended or adjusted under 35 U.S.C. 154(b) by 0 days.

(21) Appl. No.: 17/582,702

(22) Filed: Jan. 24, 2022

(65) Prior Publication Data
US 2022/0233868 A1    Jul. 28, 2022

Related U.S. Application Data

(60) Provisional application No. 63/140,557, filed on Jan. 22, 2021.

(51) Int. Cl.
| | |
|---|---|
| *A61N 1/365* | (2006.01) |
| *A61N 1/05* | (2006.01) |
| *A61N 1/36* | (2006.01) |
| *A61N 1/372* | (2006.01) |
| *A61N 1/39* | (2006.01) |

(52) U.S. Cl.
CPC ....... *A61N 1/36585* (2013.01); *A61N 1/0563* (2013.01); *A61N 1/36139* (2013.01); *A61N 1/36542* (2013.01); *A61N 1/37252* (2013.01); *A61N 1/39622* (2017.08)

(58) Field of Classification Search
CPC .............. A61N 1/36585; A61N 1/0563; A61N 1/36139; A61N 1/36542; A61N 1/37252; A61N 1/39622
See application file for complete search history.

(56) References Cited

U.S. PATENT DOCUMENTS

| | | | |
|---|---|---|---|
| 4,245,640 A | * | 1/1981 | Hunt .................... H02K 7/1876 607/33 |
| 4,870,341 A | | 9/1989 | Pihl et al. |

(Continued)

*Primary Examiner* — Brian T Gedeon
(74) *Attorney, Agent, or Firm* — William H. Dippert; Laurence A. Greenberg; Werner H. Stemer

(57) ABSTRACT

An ICD multimode system comprises a microcontroller or FPGA having a memory, a differentially driven phased array amplifier, one or more sensors, and a wireless transmitter/receiver. Based upon sensor data and demand criteria programmed into the memory, the system provides late systolic impulse (LSI) therapy to treat congestive heart failure (CHF) and ventricle level-shifting (VLS) therapy to block unwanted PVCs to prevent VT or VF dynamically and use a phased array amplifier therapy to accurately manage CRT. An external echocardiogram and ultrasound system adjusts the therapies administered based upon sensor and demand data in real time to allow a patient's heart to function at a level of improved performance and increase ejection fraction EF.

21 Claims, 8 Drawing Sheets

(56) References Cited

U.S. PATENT DOCUMENTS

| | | |
|---|---|---|
| 5,206,602 A | 4/1993 | Baumgartner et al. |
| 5,772,692 A | 6/1998 | Armstrong |
| 6,078,214 A | 6/2000 | Zhang |
| 6,430,449 B1 | 8/2002 | Hsu et al. |
| 6,438,418 B1 | 8/2002 | Swerdlow et al. |
| 6,484,059 B2 | 11/2002 | Gielen |
| 6,766,195 B1 | 7/2004 | Bomzin et al. |
| 6,968,230 B2 | 11/2005 | Waltman |
| 7,151,963 B2 | 12/2006 | Havel et al. |
| 7,200,434 B2 | 4/2007 | Havel et al. |
| 7,389,140 B1 | 6/2008 | Kroll |
| 7,450,995 B2 | 11/2008 | Moulder et al. |
| 7,555,341 B2 | 6/2009 | Moffitt et al. |
| 7,668,601 B2 | 2/2010 | Hegland et al. |
| 7,920,918 B2 | 4/2011 | Ideker et al. |
| 7,983,748 B2 | 7/2011 | Ruse |
| 7,986,992 B2 | 7/2011 | Ideker et al. |
| 8,175,702 B2 | 5/2012 | Efimov et al. |
| 8,260,416 B2 | 9/2012 | Ben-Haim et al. |
| 8,311,629 B2 | 11/2012 | Ben-Haim et al. |
| 8,509,889 B2 | 8/2013 | Efimov et al. |
| 8,538,538 B2 | 9/2013 | Goetz et al. |
| 8,560,066 B2 | 10/2013 | Efimov et al. |
| 8,639,325 B2 | 1/2014 | Efimov et al. |
| 8,798,729 B2 | 8/2014 | Kaib et al. |
| 8,874,208 B2 | 10/2014 | Efimov et al. |
| 9,067,079 B2 | 6/2015 | Efimov et al. |
| 9,526,907 B2 | 12/2016 | Efimov et al. |
| 9,561,383 B2 | 2/2017 | Ideker et al. |
| 9,757,577 B2 | 9/2017 | Ideker et al. |
| 9,839,789 B2 | 12/2017 | Kozin et al. |
| 10,500,405 B2 | 12/2019 | Walker et al. |
| 10,525,272 B2 | 1/2020 | Thompson-Nauman et al. |
| 10,532,216 B2 | 1/2020 | Tandri et al. |
| 11,052,261 B2 | 7/2021 | Tandri et al. |
| 2004/0039419 A1 | 2/2004 | Stickney et al. |
| 2004/0215258 A1* | 10/2004 | Lovett .............. A61B 5/0031 607/9 |
| 2006/0239482 A1 | 10/2006 | Hatoum |
| 2009/0157131 A1* | 6/2009 | Ideker .............. A61N 1/3918 607/5 |
| 2013/0184777 A1* | 7/2013 | Hellman ........... A61N 1/3712 607/28 |
| 2013/0284777 A1* | 10/2013 | Knight ................ F16M 13/04 248/302 |
| 2016/0101293 A1* | 4/2016 | Ideker .............. A61N 1/3937 607/4 |
| 2018/0221677 A1 | 8/2018 | Grinberg et al. |
| 2020/0368544 A1 | 11/2020 | Ideker et al. |

\* cited by examiner

MULTIMODE ICD SYSTEM COMPRISING PHASED ARRAY AMPLIFIERS TO TREAT AND MANAGE CRT, CHF, AND PVC DISORDERS USING VENTRICLE LEVEL-SHIFTING THERAPY TO MINIMIZE VT/VF AND SCA

CROSS-REFERENCE TO RELATED PATENT APPLICATION

This patent application is based upon and claims the priority of U.S. Provisional Patent Application Ser. No. 63/140,557, filed Jan. 22, 2021, incorporated herein by reference in its entirety.

FIELD OF THE INVENTION

This invention is directed to a software-controlled, amplifier-based, implantable cardiac defibrillator (ICD), linear or pulse width modulated (PWM) system. This ICD employs a cardiac pacemaker, cardiac defibrillator, cardiac resynchronization therapy (CRT), congestive heart failure (CHF) treatment, late systolic impulse (LSI) therapy for increasing ejection fraction (EF) percentage, and ventricle level shift (VLS) circuitry to block unwanted premature ventricular contractions (PVCs). In addition, an optional system employs a phased array ultrasound/echo module to provide EF data in real time that is linked via Bluetooth® technology between the ICD and the EF Module to a smart phone.

BACKGROUND OF THE INVENTION

To those physicians skilled in the art of electrophysiology and cardiac rhythm management, it is well known that ectopic beats within the ventricles (also known as premature ventricular contractions or PVCs) can and do induce ventricular tachycardia (VT) and/or ventricular fibrillation (VF). It is desirable to have a technology that can prevent some of these triggers for VF such as R on T, Long QT Syndrome, congestive heart failure (CHF), and Brugada Syndrome, or any other genetically aberrant disorder that induces an unacceptable number of PVCs per minute that may induce potentially serious or fatal arrythmias. Other benign ventricle disorders, such as irretractable ventricular bigeminy and other idiopathic causes of VT/VF, may be treated by this system as well.

During VF, the heart rate is too fast to allow adequate pumping of blood throughout the body. As evidenced on an electrocardiogram (ECG), this is approximately 300-500 excitations per minute. The chaotic characteristic of VF is not consistent with a functioning cardiovascular pump. VF may be explained in terms of highly periodic three-dimensional rotors that activate at exceedingly high rates. Such rotors may show at least two different behaviors. At one extreme they may drift throughout the heart, producing beat-to-beat changes in the activation sequence. At the other extreme, rotors may be relatively stationary, activating the ventricles at such high frequencies that the wave fronts emanating from them break up at varying distances, resulting in complex spatio-temporal patterns of fibrillatory conduction. In either case, the recorded ECG patterns are indistinguishable from VF (NCBI.LM.NIH.gov, J. Jalfe-2000, cited by 402.)

Risk factors for VF include a previous heart attack; a congenital heart defect; heart muscle disease (cardiomyopathy); any other injury that causes damage to the heart muscle; a VT circuit that causes a shift in conduction around a scarred area caused by a myocardial infarction; channelopathies; or a severe imbalance of potassium, sodium, or magnesium.

OBJECTS OF THE INVENTION

It is an object of the invention to provide an implantable cardiac system which comprises:
  a subcutaneous case capable of being positioned under a patient's skin in the pectoral area of the patient's upper left chest;
  a waveform energy control system located within the subcutaneous case, the waveform energy control system comprising:
    a microcontroller or Field Programmable Gate Array (FPGA) having a memory;
    a digital-to-analog converter (DAC); and
    differentially driven phased array amplifiers having an input and an output;
    one or more sensors;
    a wireless transmitter/receiver; and
    a battery;
  a bipolar pacing lead;
  a right ventricular pacing and defibrillation lead; and
  a left ventricular and/or cardiac synchronization (CS) pacing lead,
  wherein the left ventricle (LV) and right ventricle (RV) pacing leads deliver late systolic impulse (LSI) therapy to the patient based upon sensor data and demand criteria programmed into the memory of the microcontroller or FPGA.

It is also an object of the invention to provide an apparatus and method of treating a cardiac condition in a patient which comprises using a bipolar pacing lead and a right ventricular pacing/defibrillation lead whereby the left and right ventricular pacing leads may also deliver LSI therapy based on ECG and ultrasound sensor data, and demand criteria programmed into the memory of the microcontroller or FPGA.

It is additionally an object of the invention to provide an apparatus and method of treating a cardiac condition in a patient wherein an ultrasound ejection fraction (EF) system is capable of providing data in real time to the microcontroller or FPGA which commands the amplifiers to synchronize the RV/LV contraction timing, i.e., CRT therapy, and minimize battery drain. This therapy, in concert with LSI therapy, provides the best opportunity to increase EF for the patient.

It is a further object of the invention to provide an apparatus and method of treating a cardiac condition in a patient wherein differentially driven amplifiers deliver therapies to correct electrical issues that arise within the heart.

It is a yet further object of the invention to provide an apparatus and method of treating a cardiac condition in a patient wherein cardiac therapies are delivered using the same amplifier circuits and are commanded by the software algorithms to pace, cardiovert, defibrillate, provide ventricle level-shifting (VLS) therapy for blocking PVCs during the vulnerable period, or deliver LSI to the ventricles for the treatment of CHF, based on data from several sensors and other critical measurements. These measurements are sent to the microcontroller or FPGA and translated into commands to deliver therapies based on the type of cardiac condition.

It is a yet further object of the invention to provide an apparatus and method wherein the cardiac therapies delivered are selected from the group consisting of pacing, anti-tachycardia pacing (ATP), LSI, low/medium voltage therapy, arbitrary waveform ascending ramp shock therapy, biphasic truncated exponential (BTE) defibrillation therapy, pulseless electrical activity (PEA), and asystole rescue.

It is a yet further object of the invention to provide an apparatus and method of treating a cardiac condition in a patient whereby phase shifting the amplifier arrays differentially provides the ability to deliver very accurate CRT and pacing pulses that properly synchronize the RV and LV in terms of time difference between the contractions of the two ventricles to maximize the EF. Amplifiers have a unique capability to deliver software-regulated pulses of any shape and amplitude from the stored energy available.

It is a yet further object of the invention to provide a method of treating a cardiac condition in a patient whereby the LSI therapies are delivered during the absolute refractory period whereby the ventricles are stimulated to contract further than the heart's natural electrical system can provide and the LSI impulses are delivered during this time period to increase the EF while preventing any arrhythmia activity. The same amplifier arrays are driven differentially during this late systolic time period either from the ICD case or from a combination of LV/RV leads and an ICD case.

These and other objects of the invention will become more apparent from the discussion below.

SUMMARY OF THE INVENTION

In one aspect of the invention, a sub-threshold, negative electrical tonic stimulus and field is delivered throughout the ventricular syncytium that blocks and or inhibits PVCs during vulnerable periods, such as during the T-wave interval, which is very sensitive to any ectopic or unwanted positive stimulus. Syndromes such as Brugada, Long QT, hypertrophic cardiomyopathy and idiopathic PVCs that may trigger VF and VT compromise the patient's well-being. The negative electrical VLS stimulus may help prevent and minimize sudden cardiac arrest (SCA).

During typical action potentials, the resting potential of cardiac cells is about −90 my. When an electrical stimulus is delivered via the SA/AV conduction nodes, or a pacemaker stimulus, a depolarization occurs at around −55 my or more positive, relative to the ECG isoelectric zero volt or baseline threshold. When a normal AV node stimulus is received, the sodium channels are opened, causing a fast rise pulse in a positive deflection to produce ventricular contractions. During the vulnerable period, if an unwanted depolarization occurs, a PVC may trigger very dangerous heart rhythms such as VF that may cause sudden cardiac arrest (SCA), also known as sudden cardiac death (SCD).

In another aspect of the invention, this novel ventricle level-shifting (VLS) system generates a negative stimulus during the vulnerable period, delivered via each of the ICD wire electrodes and the ICD's phased array amplifiers, during time periods where the other pacing, CRT, or LSI are not being used, thereby blocking or inhibiting PVC activity during these vulnerable periods. The unique ventricle level-shifting (VLS) therapy is precisely managed by the same microprocessor or FPGA that controls the phased array amplifiers contained within the ICD. If a person's heart starts to experience an unacceptable number of PVCs per minute that could generate a dangerous heart rhythm, the negative ventricle level-shifting (VLS) therapies are delivered and steered from one or more electrode tips in the RV and LV through the ventricles whereby the sodium channels are biased more negative and the cells close so no action potentials can occur. The ventricle level-shifting (VLS) therapies can also conduct between any electrode or combination of electrodes and/or the ICD case which makes the potential between QRS complexes more negative (about −100 my to about −300 my). This blocks or inhibits an unwanted stimulus that could cause an abnormal heart rhythm to be initialized. This blockade and reinforcement of the −90 my resting potential could be characterized as an atraumatic, sub-threshold, tonic or change in electrical tone to a more negative bias of −100 my to about −300 my or to an even more negative voltage that may prevent PVCs from initiating or inducing VT/VF. These harmful PVCs could cause SCA. By protecting the vulnerable period during a normal heart conduction cycle and the resting periods of the heart's arithmeticity, this negative voltage therapy may prevent thousands of fatalities each year.

In yet another aspect of the invention, multiple cardiac rhythm therapies use one ICD device that contains sophisticated multi-therapy stimulus or blockades that adjust and manage abnormal heart rhythms within a human heart that can treat or adjust timing issues such as cardiac resynchronization therapy (CRT).

In a further aspect of the invention, any defibrillation ramp shock or other waveforms, such as a BTE or curved shock, may be delivered. Ramp or curved shock waveforms are safer and use less peak voltage and current per shock for cardioversion and or defibrillation than BTE shocks.

In a further aspect of the invention, LSI pulsed therapies are delivered through the left CS or any accessible artery or vein that can accomplish the CRT pacing adjustments as well as deliver the LSI therapy during the absolute refractory period to increase the ejection fraction (EF) in those patients' hearts that suffer from chronic or CHF with an abnormally low EF.

In a further aspect of the invention, an implanted device employs a beam steering, phased array, ultrasound/echo module to provide EF data in real time that is linked via wireless technology, for example, Bluetooth® technology, between the ICD and the EF Module to a smart phone or similar receiver/transmitter, such as an iPAD® or computer.

In a further aspect of the invention, a novel programmable, multi-mode, switching PWM or linear phased array amplifiers are based within an ICD system that provides several software controlled cardiac treatment therapies, including pacing, ATP, cardioversion, arbitrary waveform ascending ramp or BTE defibrillation therapy, CHF using LSI, and/or manual or dynamic therapies in real time. In this embodiment, the focus is on treatment methods to prevent the PVCs that could trigger unwanted ventricular heart rhythms. It is proposed to use a low-voltage, low-current electrical field to provide a sub-threshold, tonic therapy that level-shifts the syncytium of the ventricles (VLS) to a more negative state relative to the natural resting voltage of −90 my, where all ventricle sodium channels are closed and are at an absolute refractory state, and where no action potentials can be initiated. In the case of Long QT, Brugada, or excessive PVCs, the device will level-shift the syncytium to a more negative state at approximately −100 my to −300 my or more negative to prevent PVCs from initiating. The intent is to prevent PVCs from interfering with the normal cardiac cycle by applying the voltage on a more negative bias, thereby possibly reducing sensitivity that could lead to the problematic triggers that induce VT/VF. This therapy can be carefully timed between the QRS complexes so it does not interfere with normal cardiac conduction, and the same circuitry can deliver pacing, defibrillation shocks, CRT, LSI, CHF, etc. It may even be useful to capture an episode of VF induced by any modality and extinguish the chaotic VF wavefronts caused by unstable sodium channels.

In a further aspect of the invention, a novel programmable, multi-mode, switching PWM or linear phased array amplifiers are based upon an ICD system that provides several software controlled cardiac treatment therapies, including pacing, ATP, cardioversion, arbitrary waveform ramp or BTE defibrillation therapy, and CHF using LSI and/or manual or dynamic therapies in real time. A phased array ultrasound/echo EF module communicates via wireless technology, for example, Bluetooth technology, with an ICD and a smart phone (such as an iPHONE®) or a similar device whereby several therapies can be adjusted using software algorithm commands. One universal electronic circuit design is used to treat multiple cardiac conditions by delivering selected software commands that automatically provide flexibility and efficiency to treat patients with cardiac issues and diseases.

The individual cells of the heart communicate with each other through gap junctions via electrical signals, which are disrupted in those patients with Brugada Syndrome. This syndrome is caused by genetic mutations in a person's DNA. The first mutations described in association with Brugada were in a gene responsible for a protein, or ion channel, that controls the flow of sodium ions through the cell membrane of heart muscles—the cardiac sodium channels. The possible effect of Brugada Syndrome is a chaotic electrical storm, specifically involving the RV outflow tract, and PVCs that may induce monomorphic VT or polymorphic VT in the LV and RV. The goal is to treat and prevent the PVC episodes by ventricle level shifting the resting (vulnerable) period of –90 my or much more negative, as an atraumatic, sub-threshold, tonic delivery system. This may help manage Brugada and possibly prevent VT/VF.

In a further aspect of the invention, an implantable cardiac system comprises:
  a subcutaneous case capable of being positioned under a patient's skin in the pectoral area of the patient's upper left chest;
  a waveform energy control system located within the subcutaneous case, the waveform energy control system comprising:
    a microcontroller or FPGA having a memory;
    a digital-to analog converter (DAC);
    differentially driven phased array amplifiers having an input and an output;
    one or more sensors;
    a wireless transmitter/receiver; and
    a battery;
  a bipolar pacing lead;
  a right ventricular pacing and defibrillation lead; and
  a left ventricular and/or coronary sinus (CS) pacing lead,
  wherein the LV and RV pacing leads deliver LSI therapy to the patient based upon sensor data and demand criteria programmed into the memory of the microcontroller or FPGA.

In a further aspect of the invention, an implantable cardiac system comprises:
  a subcutaneous case capable of being positioned under a patient's skin;
  a waveform energy control system located within the subcutaneous case, the waveform energy control system comprising:
    a microcontroller or FPGA having a memory;
    differentially driven phased array amplifiers having an input and an output;
    a wireless Bluetooth transmitter/receiver;
    a battery; and
    one or more sensors;
  a bipolar pacing lead;
  a right ventricular (RV) pacing and defibrillation lead; and
  a left ventricular (LV) and/or coronary sinus (CS) pacing lead,
  wherein the LV pacing lead and the RV pacing lead deliver cardiac therapy to a heart of a patient based upon sensor data and demand criteria programmed into the memory of the microcontroller or FPGA.

In a further aspect of the invention, an implantable cardiac system also comprises an optional, substernal ultrasound ejection fraction (EF) module capable of instructing the microcontroller or FPGA in real time to maximize the EF.

In a further aspect of the implantable cardiac system of the invention, the differentially driven phased array amplifiers are capable of being driven to deliver medically useful current vectors to the patient's heart using any voltage and/or arbitrary ramp waveforms for a medically useful cardiac therapy.

In a further aspect of the implantable cardiac system of the invention, the microcontroller or the FPGA are part of a System on a Chip (SOC).

In a further aspect of the implantable cardiac system of the invention, the sensors are selected from the group consisting of an $O_2$ sensor, an ECG, an inclinometer, and an accelerometer, which provide feedback to the microcontroller or FPGA so that delivered voltage and current therapies can be efficiently delivered based on demand.

In a further aspect of the implantable cardiac system of the invention, the cardiac therapy is delivered using the same phased array amplifiers and is commanded by software algorithms within the memory to pace, cardiovert, defibrillate, or deliver late systolic impulses (LSI) to the ventricles for the treatment of congestive heart failure (CHF), by increasing the EF based on data from one or more sensors that are translated into commands to deliver therapies.

In a further aspect of the implantable cardiac system of the invention, the cardiac therapy delivered is selected from the group consisting of pacing, ventricle level shift (VLS) therapy, premature ventricular contractions (PVC) block therapy, anti-tachycardia pacing (ATP) therapy, congestive heart failure (CHF) therapy, cardiac resynchronization therapy (CRT), late systolic impulses (LSI) therapy, low voltage/medium voltage (LV/MV) therapy, arbitrary waveform ramp shock therapy, biphasic truncated exponential (BTE) defibrillation therapy, and pulseless electrical activity (PEA) asystole rescue.

In a further aspect of the implantable cardiac system of the invention, ventricle level-shifting (VLS) software and hardware within the ICD deliver a negative bias voltage during vulnerable periods between QRS complexes that blocks or inhibits unwanted premature ventricular contractions (PVCs) from triggering ventricular tachycardia (VT)/ventricular fibrillation (VF) that may cause sudden cardiac arrest (SCA).

In a further aspect of the implantable cardiac system of the invention, the phased array amplifiers can be phase-shifted differentially to deliver very accurate cardiac resynchronization therapy (CRT) and pacing pulses that properly synchronize the right ventricle (RV) and left ventricle (LV) in terms of time difference between the two ventricles' contractions to maximize the ejection fraction (EF) and the phased array amplifiers have a unique ability to deliver software regulated and delivered pulses of any shape and amplitude from any stored voltage energy source.

In a further aspect of the implantable cardiac system of the invention, the late systolic impulses (LSI) therapy is delivered during an absolute refractory period whereby the ventricles are stimulated to contract further than the heart's natural electrical system can deliver and the LSI impulses are delivered during this time period to increase the ejection fraction (EF) while preventing any arrhythmia activity and the same phased array amplifiers are driven differentially during this late systolic time period from the ICD or driven differentially from a combination of left ventricular (LV)/right ventricular (RV) ICD leads and/or between the ejection fraction (EF) module phased array amplifiers to increase the ejection fraction and improve a congestive heart failure (CHF) condition.

In a further aspect of the implantable cardiac system of the invention, a digital-to-analog converter (DAC) is operatively connected to the input of the differentially driven phased array amplifier circuits, the microcontroller or FPGA is configured to respond to software commands to generate signals to the DAC, the DAC provides signals to the input of the differentially driven phased array amplifier circuits, and the output of the differentially driven phased array amplifier circuits delivers constant current, constant voltage, or constant energy ascending arbitrary ramp waveforms, BTE waveforms, or ascending arbitrary ramp or curved waveforms for pacing, ATP, low-voltage therapy, defibrillation, or cardioversion electrical shocks to the patient's heart.

In a further aspect of the implantable cardiac system of the invention, the system comprises a magnetic power supply that uses body motion to assist in charging the battery module and that delivers voltage and current on demand as required by the ICD and/or the ejection fraction (EF) module.

In a further aspect of the implantable cardiac system of the invention, the system also comprises a Bluetooth wireless transmitter/receiver or similar device external to the patient.

In a further aspect of the implantable cardiac system of the invention, there is Bluetooth connectivity between the subcutaneous case and the external transmitter/receiver; optionally between the subcutaneous case and the substernal ejection fraction (EF) module; and optionally between the EF module and the external transmitter/receiver.

In a further aspect of the invention, a method of treating a cardiac condition in a patient comprises implanting an implantable cardiac system described herein in a patient and applying the appropriate treatment to the patient.

In a further aspect of the method of the invention, the cardiac condition treated is congestive heart failure, ventricular tachycardia, or ventricular fibrillation.

In a further aspect of the method of the invention, the appropriate treatment is pacing, ventricle level-shifting (VLS) therapy, premature ventricular contractions (PVC) block therapy, anti-tachycardia pacing (ATP) therapy, congestive heart failure (CHF) therapy, cardiac resynchronization therapy (CRT), late systolic impulses (LSI) therapy, low voltage/medium voltage (LV/MV) therapy, arbitrary waveform ramp shock therapy, biphasic truncated exponential (BTE) defibrillation therapy, or pulseless electrical activity (PEA) asystole rescue.

In a further aspect of the invention, a system also comprises an ultrasound ejection fraction (EF) system capable of being adjusted in real time to maximize the EF and minimize battery drain.

In a further aspect of the invention, the differentially driven phased array amplifiers are capable of being driven to deliver medically useful current vectors to the patient's heart using any voltage and/or arbitrary ramp waveforms for a medically useful therapy.

In a further aspect of the invention, in the system the sensors are selected from the group consisting of an $O_2$ sensor, an ECG, an inclinometer, and an accelerometer to provide data back to the microcontroller. The $O_2$ sensor provides data on the patient's blood oxygen level, the ECG displays rhythm information for potential therapies, the inclinometer indicates whether the patient is recumbent, sitting, standing, or exercising (walking, climbing stairs, etc.). The accelerometer provides additional information regarding the exercise, indicating the intensity of activity. Software will determine what level of LSI the patient needs dynamically. This is a demand-based system with an emphasis on minimizing battery usage so the device does not require frequent external charging of the batteries.

In a further aspect of the invention, cardiac therapies are delivered using the same phased array amplifiers and are commanded by software algorithms within the memory to pace, cardiovert, defibrillate, or deliver LSI to the ventricles for the treatment of CHF, by increasing the EF based on data from one or more sensors and other critical measurements that are translated into commands to deliver therapies based on what type of cardiac condition or conditions are required.

In a further aspect of the invention, the cardiac therapies delivered are selected from the group consisting of pacing, ATP, LSI, low voltage/medium voltage therapy, arbitrary waveform ramp or curved shock therapy, BTE defibrillation therapy, and pulseless electrical activity (PEA) asystole rescue.

In a further aspect of the invention, in the system the phased array amplifiers can be phase shifted differentially to provide the ability to deliver very accurate CRT and pacing pulses that properly synchronize the RV and LV in terms of time difference between the contractions of the two ventricles to maximize the EF. Phased array amplifiers have a unique ability to deliver software regulated and delivered pulses of any shape and amplitude from the stored energy available.

It is a yet further object of the invention to provide a method of treating a cardiac condition in a patient whereby the LSI therapies are delivered during the absolute refractory period whereby the ventricles are stimulated to contract further than the heart's natural electrical system can provide, and the LSI impulses are delivered during this time period to increase the EF while preventing any arrhythmia activity. The same phased array amplifiers are driven differentially during this late systolic time period either from the ICD case only or driven differentially from a combination of LV/RV leads and ICD case.

In a further aspect of the invention, the microcontroller or FPGA is operatively connected to the DAC, the DAC is operatively connected to the input of the differentially driven phased array amplifier circuits, the microcontroller or FPGA is configured to respond to software commands to generate signals to the DAC, the DAC provides signals to the input of the differentially driven phased array amplifier circuits, and the output of the differentially driven phased array amplifier circuits delivers constant current, constant voltage, or constant energy ascending arbitrary waveforms, BTE waveforms, or ascending arbitrary waveforms for pacing, ATP, low-voltage therapy, defibrillation, or cardioversion electrical shocks to the patient's heart.

In a further aspect of the invention, the system also comprises a wireless transmitter/receiver external to the patient's body.

In a further aspect of the invention, there is Bluetooth connectivity in the system.

In a further aspect of the invention, a method of treating a cardiac condition in a patient comprises implanting an ICD comprising a subcutaneous case having a waveform energy control system, one or more sensors, and a wireless Bluetooth transmitter/receiver; a bipolar pacing lead; an RV pacing and ventricular defibrillation lead; and a left CS pacing lead.

In a further aspect of the method of the invention, the left CS pacing lead delivers LSI therapy to the patient's heart based upon sensor data and demand criteria programmed into the memory of the microcontroller.

DETAILED DESCRIPTION OF THE DRAWINGS

Figure 1:
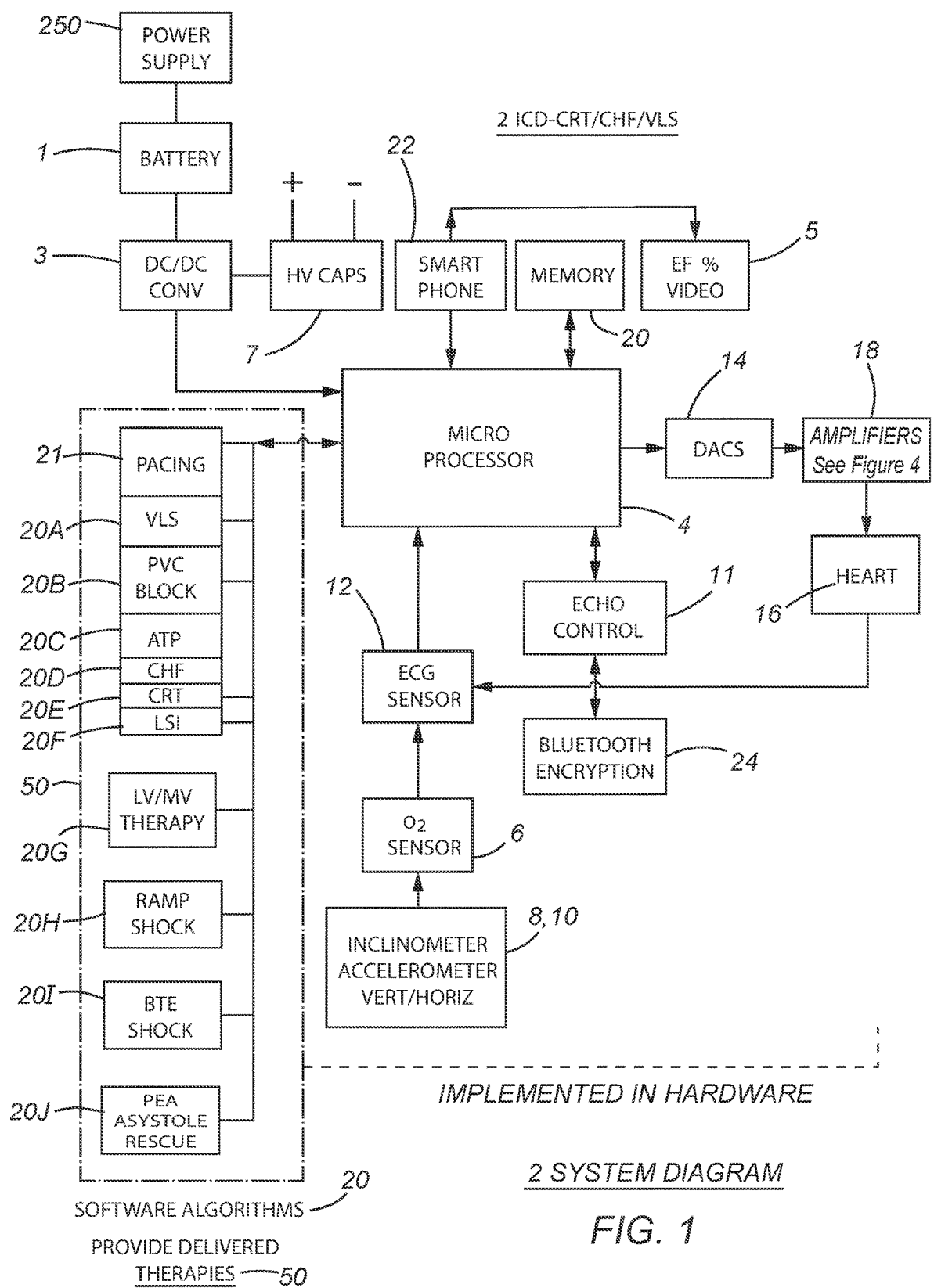
FIG. 1 is a block diagram that represents one aspect of the invention, showing the delivered functions provided through software algorithms implemented in the ICD hardware.

FIG. 1 is a block diagram of an ICD-CRT/CHF/VLS system 2 according to the invention wherein a microprocessor/microcontroller or FPGA 4 receives user commands from electrophysiologists (EP MDs, not shown), where software protocols are selected and delivered using data from sensors such as O$_2$ sensor 6, inclinometer 8, accelerometer 10, and ECG sensor 12. Command signals are sent through digital-to-analog converters (DACs) 14. The signals are then delivered through or to a patient's heart 16 via differentially driven phased array amplifiers 18 to automatically or manually correct or manage one or more cardiac conditions as shown in the listing 20 of software algorithms for ventricle level shifting (VLS) 20A, PVC blocking 20B, ATP 20C, CHF 20D, CRT 20E, LSI 20F, LV/MV therapy 20G, ramp shock 20H, BTE shock 20I, PEA asystole rescue 20J, and pacing 21, which are programmed for different treatment purposes. A smart phone 22, such as an iPHONE, is connected via Bluetooth technology 24 and/or echo control 11 so that sensor data, including data from ECG 12, ejection fraction (EF) percentage 5 as well as O$_2$ sensor 6, inclination sensor 8, acceleration sensor 10, and any other desired parameter may be displayed on the screen of smart phone 22 and/or be linked with an EP MD for interpretation and evaluation. Inclination and acceleration sensors 8, 10 indicate that there is a posture and/or activity change in real time which may require an automatic adjustment of the LSI impulses which increases the EF percentage 5. The software algorithms 20 correspond to delivered therapies.

Figure 2:
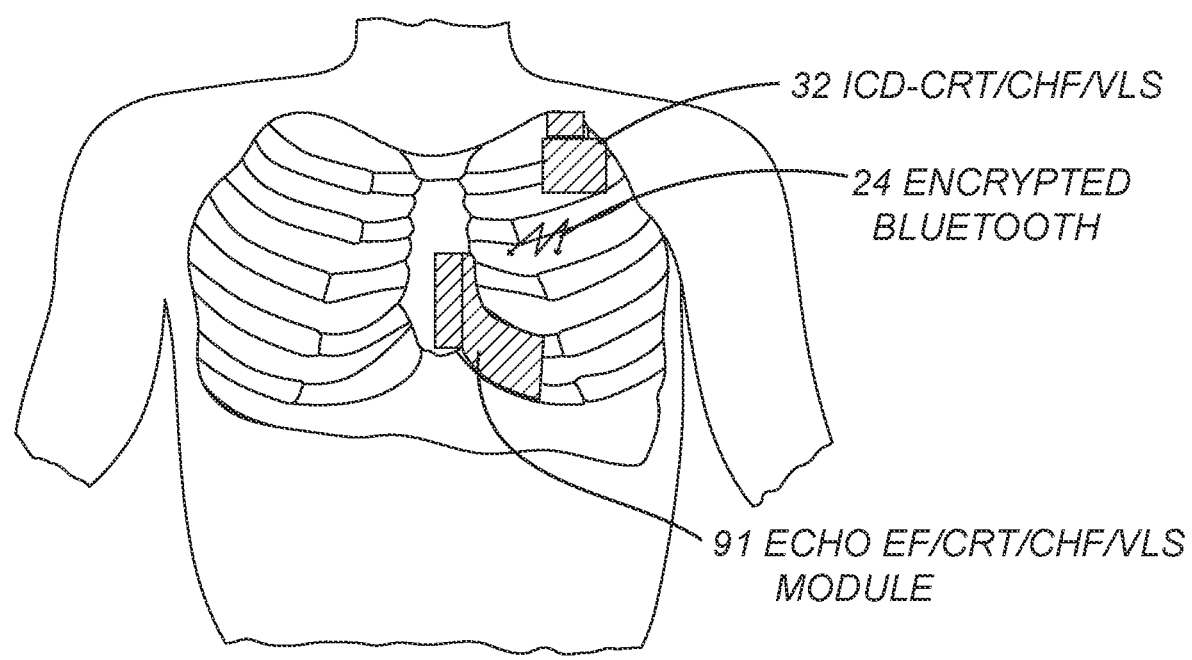
FIG. 2 represents the placement positions of a subcutaneous ICD and an optional Echo/ultrasound EF/CRT/CHF/VLS module located substernally in the chest of a patient according to the invention.

FIG. 2 represents the substernal placement of an Echo EF/CRT/CHF/VLS module 91 as well as a subcutaneous ICD-CRT/CHF/VLS device 32. Communications between the ICD-CRT/CHF/VLS device 32 and the Echo EF/CRT/CHF/VLS module 91 are encrypted and accomplished by using a Bluetooth bidirectional protocol 24.

Figure 3:
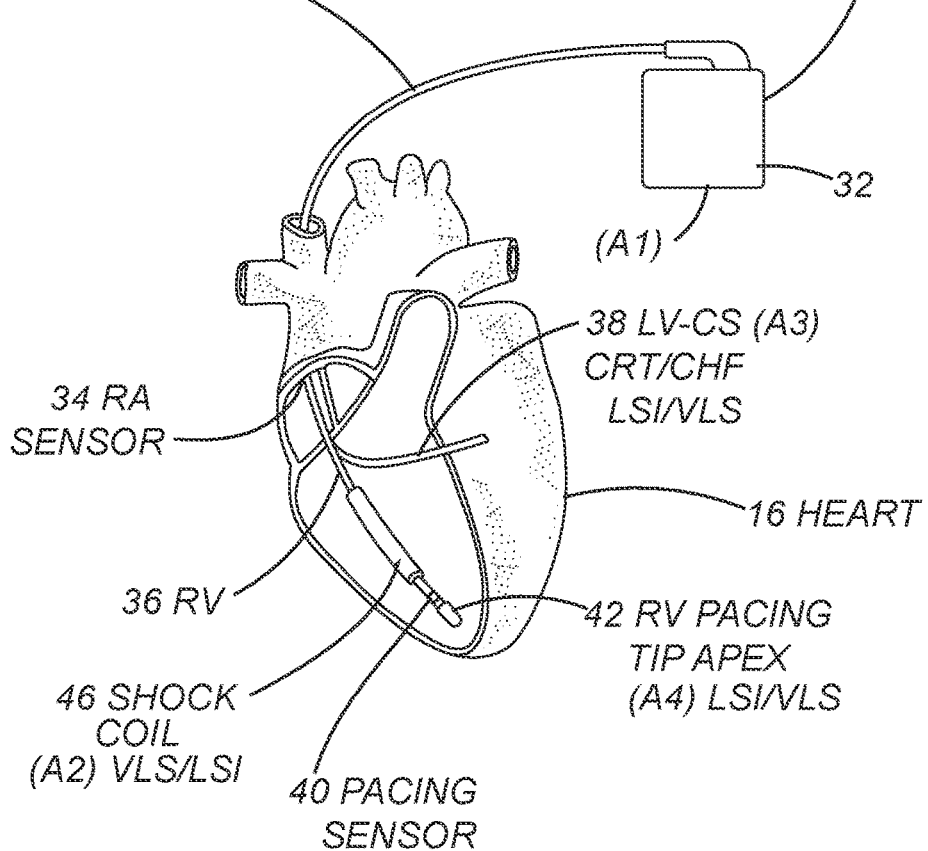
FIG. 3 represents the placement of lead set 30 and electrodes from an ICD-CRT/CHF/VLS module in a patient's heart according to the invention.

FIG. 3 represents placement of the typical lead set 30 comprising wires for the right atrial (RA) sensor/pacing 34, right ventricle (RV) lead wire 36, sensor band 40, RV pacing tip apex (A4) 42, RV shock coil (A2) 46, and left ventricle (LV) or coronary sinus (CS) (A3) lead wire 38. The lead set wires 30, which are bundled together in CRT/CHF/VLS bipolar pacing RV/LV shock coil lead set 32, provide different modes of electrical therapies using the same lead wires within the heart 16 to manage or correct certain cardiac rhythm disorders:

(1) In the cardiac resynchronization therapy (CRT) mode the pacing pulses synchronize the LV and RV in terms of contraction timing, which increases the EF and makes the heart 16 pump more efficiently.

(2) In the congestive heart failure/late systolic impulses (CHF/LSI) mode late systolic impulses are provided which are delivered through the RV and LV for the purpose of increasing the ventricle contraction forces, which then increases the ejection fraction (EF) within the heart 16.

(3) In the ventricle level shifting (VLS) mode a negative low voltage, low current, steerable, atraumatic subthreshold electrical field or tonic negative electrical therapy is delivered that level shifts the ventricles' cells from the normal resting voltage of about −90 mv to a more negative voltage from about −100 mv to about −300 mv, for the purpose of preventing and/or blocking unwanted premature ventricular contractions (PVCs) during the vulnerable time periods that may induce VT/VF or SCA. The negative voltages may be steady state DC voltages or pulsed or stepped voltages using any arbitrary waveforms to deliver the negative voltage level shifting (VLS) therapies.

(4) ICD-CRT/CHF/VLS 32 comprises a hot can that provides another amplifier (A1) as a vector steering point wherein the other three amplifiers (A2), (A3), and (A4) may all provide current paths between each other and the (A1) hot can to deliver the many cardiac therapies as required from the sensors 6, 8, 10, 12 and microcontroller circuitry 4.

Figure 4:
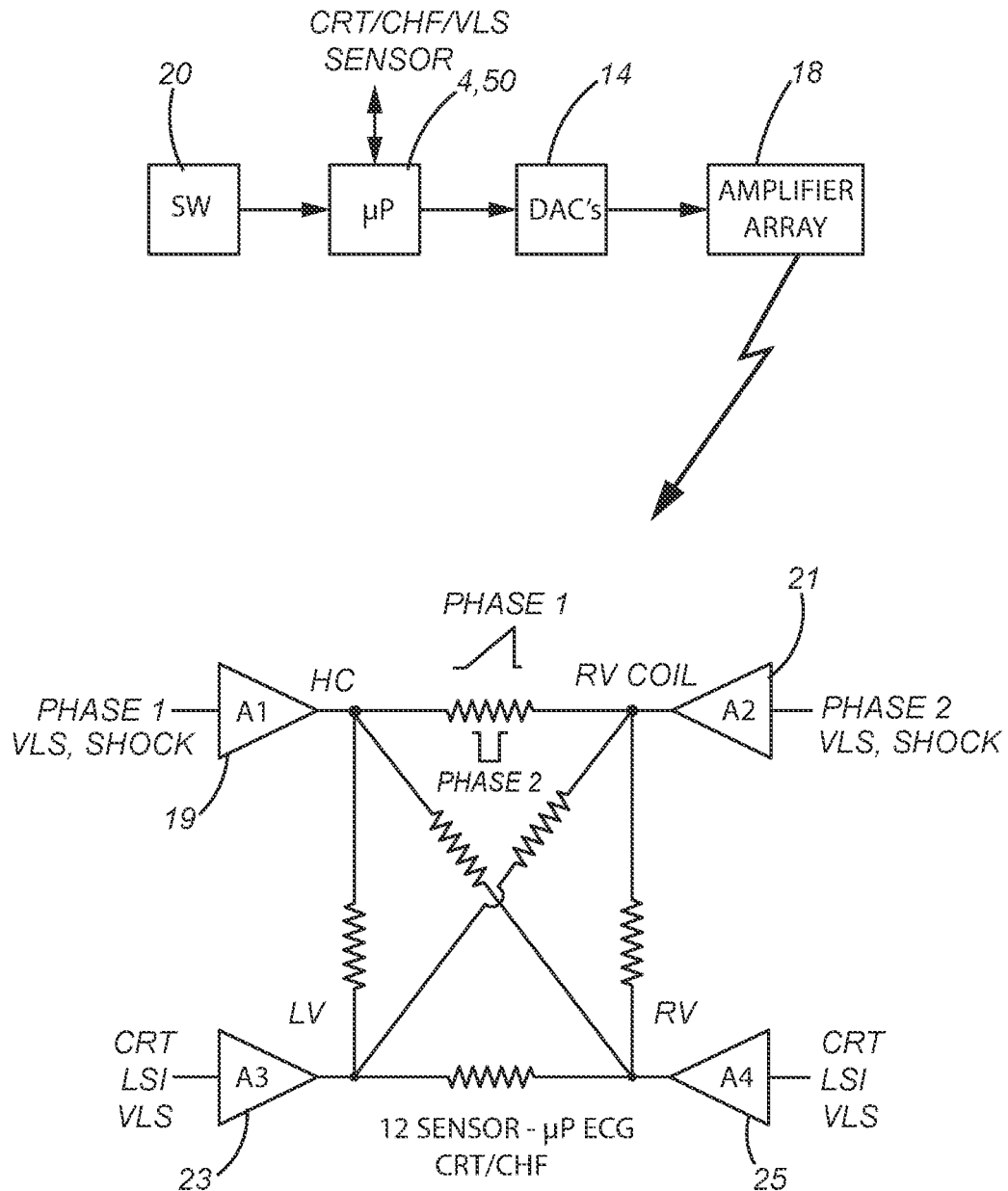
FIG. 4 is a schematic representation of the functional blocks and phased array amplifier circuitry of one aspect of the invention.

FIG. 4 represents a schematic using differentially driven phased array amplifiers 18 wherein all the various cardiac therapies are delivered using the same phased array amplifier circuits 19, 21, 23, 25. The phased array amplifier circuits 19, 21, 23, 25 are commanded by the software algorithms 20 to pace, ventricle level shift (VLS), cardiovert or defibrillate, deliver late systolic impulse (LSI) to the right and left ventricles (RV/LV) or the treatment of congestive heart failure (CHF) by increasing the EF based on several sensors' data as sampled by the O$_2$ sensor 6, inclinometer 8, accelerometer 10, ECG 12, and other critical measurements that are translated into commands to deliver therapies 50 based on what type of cardiac condition(s) are required. Defibrillation and/or cardioversion shocks are delivered via amplifiers (A1) and (A2) by delivering high, medium, or low voltage shocking waveforms such as ascending ramp or BTE or square waveforms or any ascending curved arbitrary waveform that may be useful to defibrillate or cardiovert successfully.

In another embodiment of the invention shown in FIGS. 5 and 6, a multi-layer, substernal rigid/flexible circuit EF-CHF-CRT-VLS assembly 91 is surgically installed below the sternum 66 and will traverse toward the upper portion of the heart 16. A flexible circuit assembly 60 will contain one or more ICD-type batteries in a battery module 62 and associated electronics 64. Contacts or electrodes A1 68 and A2 70 will be on the distal side of a flexible circuit 80 and will be in contact with the RV of the heart 16.

Figure 5:
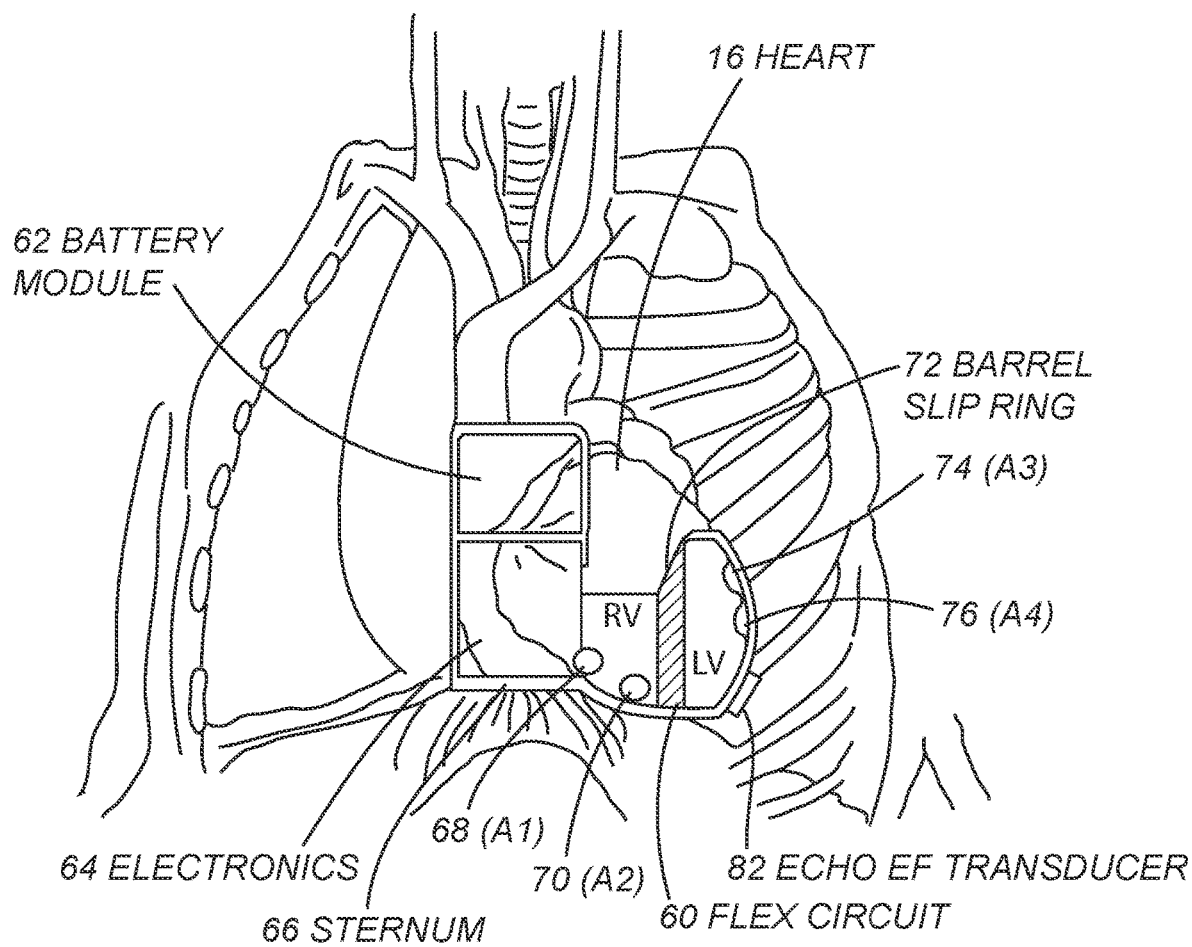
FIG. 5 is a representation of a multi-layer, substernal EF-CHF-CRT-VLS device according to the invention.
Figure 6:
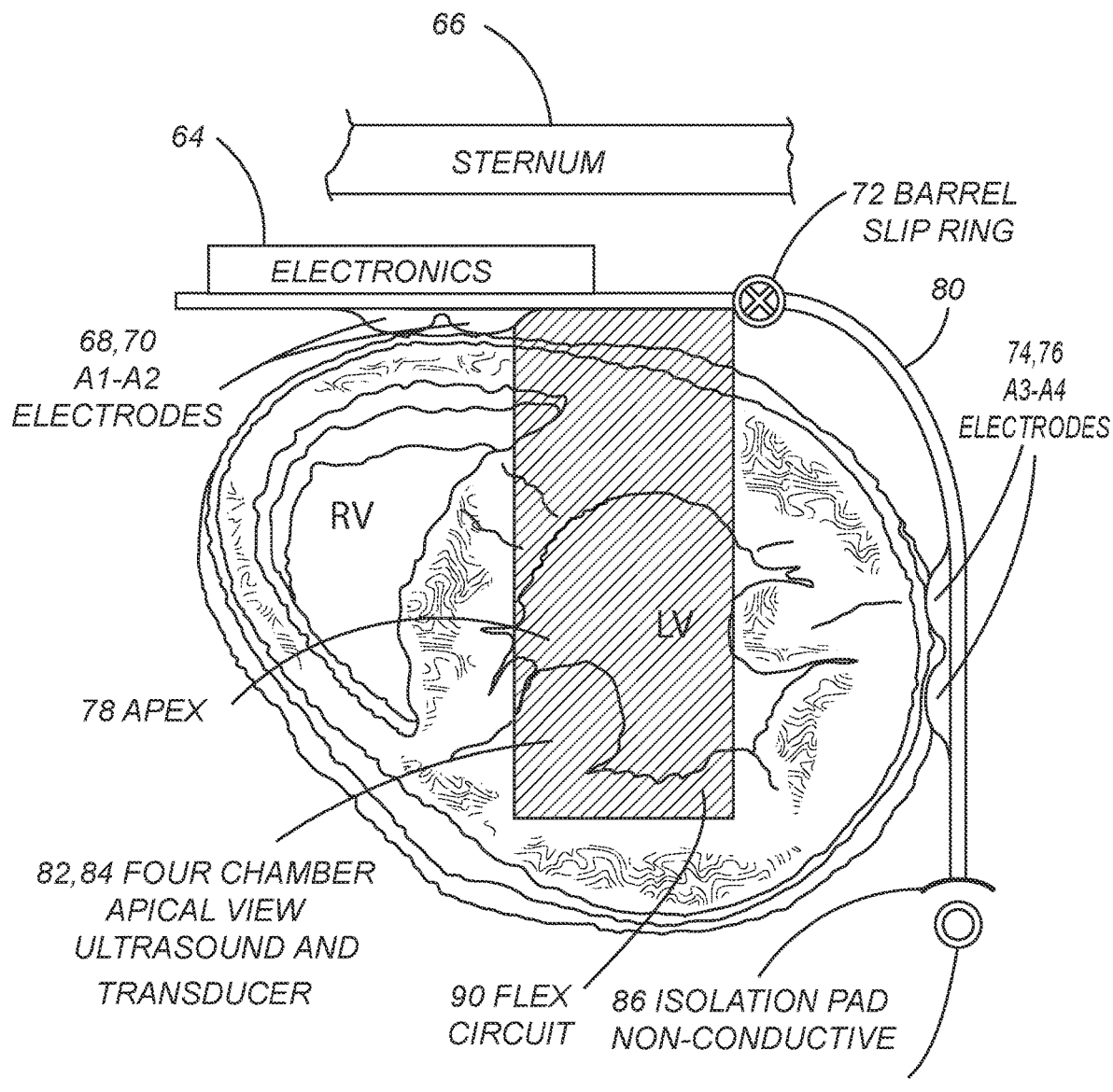
FIG. 6 is a cross-sectional view of a multi-layer, substernal EF-CHF-CRT-VLS device depicting an ultrasound transducer focused at the apex of the heart for the purpose of providing an apical four chamber echocardiogram view on a smart phone, according to the invention.

In FIG. 6, a further embodiment of the invention is shown which is a rotated view of FIG. 5. The assembly 91 will project toward the LV through a barrel slip ring 72, with a precise tension adjustment provided within barrel slip ring 72, allowing for flexible circuit 80 and contacts or electrodes A3 74 and A4 76 to form around and be in contact with the LV of the heart 16.

Between electrode A2 70 and barrel slip ring 72, there is a flexible circuit 90 that folds over the depth of the heart 16 and is in contact with or in close proximity to the apex 78 of the heart 16. Transducer 82, which is part of the flexible circuit 90, transmits and receives ultrasound signals driven by the electronics 64 to produce an echocardiogram/ultrasound image of the four chamber apical view 84. Care should be taken to not interfere with the phrenic nerve 86 by employing a non-conductive isolation pad 88.

Figure 7A:
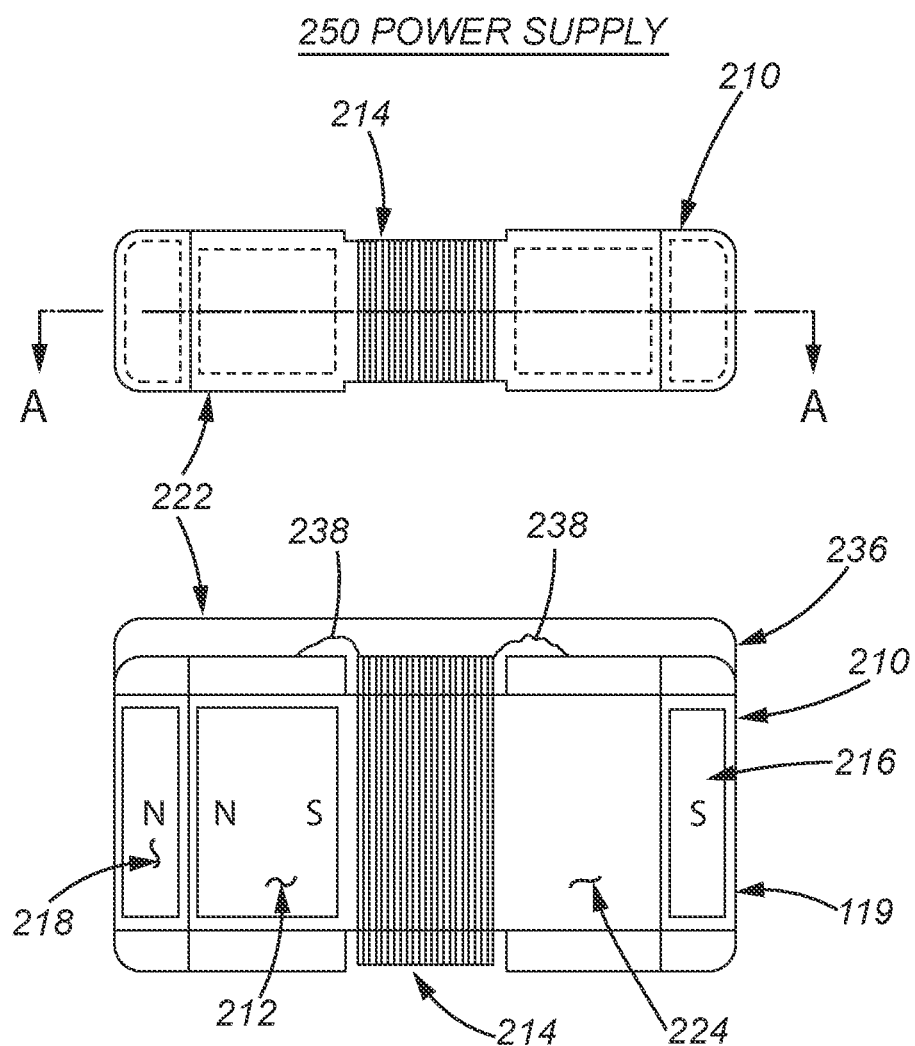
FIG. 7A is a representation of a cross-sectional view of a magnetic power supply that uses body motion to assist in charging the battery module and/or that delivers voltage and current on demand as required by the devices according to the invention.
Figure 7B:
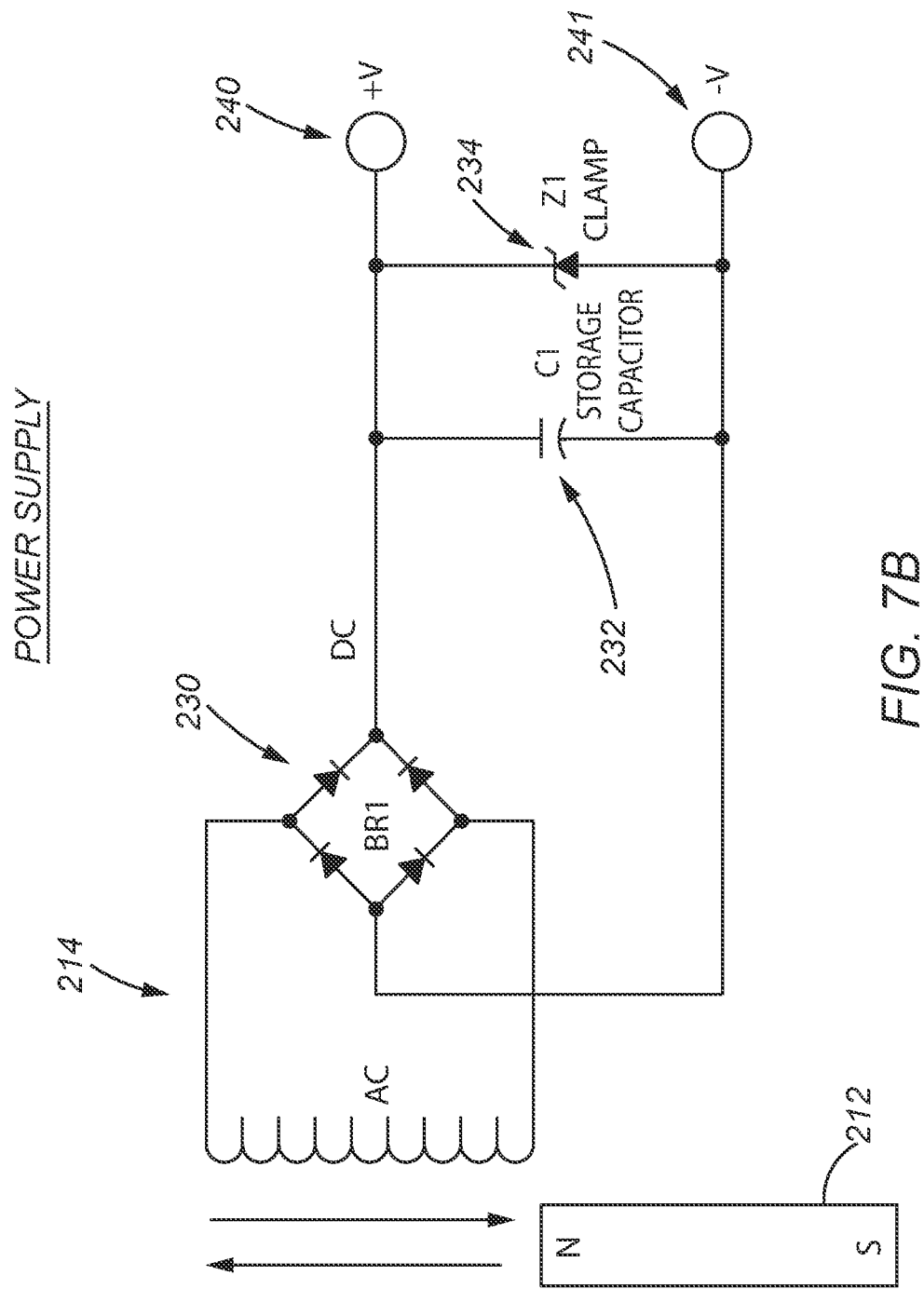
FIG. 7B is a schematic representation of an AC to DC power supply useful according to the invention.

FIGS. 7A and 7B represent embodiments of a magnetic power supply 250 that does not require batteries. The magnetic power supply 250 comprises a case 222 wherein a traversing or flying magnet 212 that, pursuant to Faraday's Law of Electromotive Force (EMF), creates an electrical potential or voltage by moving the traversing magnet 212 through a coil 214 of wire with a specified number of turns. The traversing magnet 212 is captured in a cavity within case 222 between two other magnets which are installed in fixed positions to have their fields aligned as repelling magnets 216, 218 for the traversing magnet 212. On one end of the device the north pole of a fixed magnet 218 will be opposing the north pole of the traversing magnet 212, and on the opposite end of the device the south pole of the fixed magnet 216 will be opposing the south pole of the traversing magnet 212. This arrangement provides a traversing magnet 212 which will traverse or fly between both opposing fields within the device cavities without hitting the internal end walls of the case 222. Magnetic poles or fields which are the same will repel and magnetic poles or fields which are opposites will attract. The traversing magnet 212 shall have a coating of polytetrafluoroethylene or a similar material to reduce friction to near zero within the traversing chamber 224. As the traversing magnet 212 is propelled by any movement, including walking, running or any other motion in the vectored direction of the device, the traversing magnet 212 passes through the wire coil 214 as shown in FIGS. 7A and 76. The repelling magnets 216, 218 aid in the near perpetual motion of the traversing magnet to provide a DC voltage even when a person is at rest but making subtle movements. This action produces an electrical alternating current AC which is then rectified through BR1 230 into a direct current DC. The DC voltage is then filtered by C1 storage capacitor 232 to remove any AC ripple and is also used as a storage device and keeps the DC voltage stable and quiet from noise to power the charging-power supply. Zener diode Z1 234 is used as an electrical clamp to keep the maximum voltage limited to a value expected to be from about +5 VDC to about +12 VDC. These components are housed in the electronics cavity 236. Coil wires 238 extend from wire coil 214 into electronics cavity 236. When the heart is at a resting rate of from about 60 to about 80 beats per minute, any body movement will produce stored energy. These voltages provide energy storage in a "super capacitor" which can be used to either power the LSI therapy and/or charge the batteries associated with the ICD 32 and/or ultrasound echocardiogram device. The positive electrode 240 and negative electrode 241 are shown for reference only. Power supply 250 requires no maintenance and may assist the charging of batteries and/or delivery of voltage and current on demand as required by the devices.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An implantable cardioverter defibrillator (ICD) system for administering cardiac therapy to a patient, which comprises:
    a subcutaneous case capable of being positioned under a patient's skin and in communication with the patient's heart;
    an arbitrary waveform control system located within the subcutaneous case, the arbitrary waveform control system comprising:
        a microcontroller or FPGA having a memory;
        differentially driven phased array amplifiers comprising hot can amplifier A1 and amplifiers A2, A3, and A4;
        a wireless transmitter/receiver; and
        a battery;
    one or more sensors;
    a bipolar pacing lead to be positioned in a right ventricle (RV) of the patient's heart and in functional communication with amplifier A4;
    a right ventricular (RV) pacing and shocking coil/defibrillation lead in functional communication with amplifier A2; and
    a left ventricular (LV) and/or coronary sinus (CS) pacing lead in functional communication with amplifier A3,
    wherein the bipolar pacing lead, amplifier A4, the right ventricular (RV) pacing and shocking coil/defibrillation lead, amplifier A2, the left ventricular (LV) and/or coronary sinus (CS) pacing lead, and amplifier A3 form a triangular electrical field, and
    wherein, based upon sensor data and demand criteria software programmed into the memory of the microcontroller or FPGA, the bipolar pacing lead, the right ventricular pacing and shocking coil/defibrillation lead, and the left ventricular and/or coronary sinus pacing lead deliver cardiac therapy to the patient's heart.

2. The system of claim 1, wherein the differentially driven phased array amplifier circuits deliver constant voltage or constant current ascending arbitrary ramp or curved waveforms, BTE waveforms, for defibrillation, or cardioversion electrical shocks to the patient's heart which are capable of being driven to deliver medically useful, dynamically steered current vectors to the patient's heart using any voltage and/or arbitrary ramp or curved waveforms for a medically useful cardiac therapy.

3. The system of claim 1, wherein the sensors are selected from the group consisting of an $O_2$ sensor, an ECG, an inclinometer, and an accelerometer, which provide feedback to the microcontroller or FPGA.

4. The system of claim 1, wherein the cardiac therapy is delivered using the same phased array amplifiers and is commanded by software algorithms within the memory to pace, cardiovert, defibrillate, or deliver late systolic impulses (LSI) to the ventricles for the treatment of congestive heart failure (CHF) to increase ejection fraction (EF) by increasing the force of LV/RV contractions, during the absolute refractory period within the QRS complex, based on data from one or more sensors that are translated into commands to deliver therapies.

5. The system of claim 1, wherein ventricle level shifting (VLS) software in the microcontroller or FPGA and hardware within the ICD system that delivers an atraumatic, sub-threshold, tonic negative bias voltage during vulnerable periods between QRS complexes that blocks or inhibits premature ventricular contractions (PVCs) from triggering ventricular tachycardia (VT)/ventricular fibrillation (VF) that may cause sudden cardiac arrest (SCA).

6. The system of claim 1 which comprises an implanted internal magnetic power supply that uses body motion to assist charging the battery and/or delivers voltage and current on demand as required by the ICD system.

7. The system of claim 1, wherein in a cardiac resynchronization therapy (CRT) mode the phased array amplifiers are phase shifted differentially to deliverer accurate CRT pulses that properly synchronize a right ventricle (RV) and a left ventricle (LV) with regard to time difference between force contractions of the two ventricles to maximize the ejection fraction (EF) wherein the phased array amplifiers deliver software commanded, electronically regulated voltage and current arbitrary pulses of any shape and amplitude from stored energy available to deliver accurate CRT therapy as well as to deliver LSI for CHF in which the combined therapies of CHF and CRT increase EF to benefit the patient.

8. The system of claim 1, wherein in a congestive heart failure (CHF)/late systolic impulse (LSI) mode late systolic impulses are provided during the absolute refractory period of the QRS complexes which are delivered through the RV and LV for the purpose of increasing the ventricle contraction forces, which then increase the ejection fraction (EF) within the patient's heart.

9. The system of claim 1, wherein in a ventricle level shifting (VLS) mode a negative low voltage, low current, steerable, atraumatic sub-threshold electrical field or tonic, negative electrical therapy is delivered that level shifts cells of the ventricles from a normal resting voltage of about −90 mV as referenced to the isoelectric line or zero voltage base line ECG to a more negative voltage from about −100 mV to about −300 mV to prevent and/or block premature ventricular contractions (PVCs) during vulnerable time periods during a T wave interval that may induce VT/VF or SCA.

10. The system of claim 9, wherein the negative voltages may be DC voltages or pulsed or stepped voltages using arbitrary waveforms to deliver the negative voltage ventricle level shifting (VLS) therapies.

11. The system of claim 1, wherein the waveform energy control system further comprises a hot can (HC) that provides an amplifier A1 as a vector steering surface and wherein the phased array amplifiers comprise three amplifiers A2, A3, and A4 that provide current paths between each other and the hot can (HC) amplifier A1 to deliver cardiac therapy through the entire syncytium of the ventricles whereby the same four amplifiers may deliver therapies at different time periods that treat several different conditions.

12. The system of claim 1, wherein an inclinometer and/or an accelerometer indicates that there is a posture and/or activity change in real time which induces an automatic adjustment of the LSI impulses to treat CHF which increases the ejection fraction (EF) percentage, and physiological changes within the ECG are adjusted for situations that require electrical correction to improve cardiac output efficiency.

13. A method of treating a cardiac condition in a patient, which comprises implanting an implantable cardiac system of claim 1 into the patient and delivering appropriate treatments to the patient.

14. The method of claim 13, wherein the cardiac condition treated is R on T phenomenon, Long QT Syndrome, congestive heart failure (CHF), low EF, ventricular tachycardia (VT), ventricular fibrillation (VF), Brugada Syndrome, any other idiopathic or genetically aberrant disorder that induces an unacceptable number of PVCs per minute that induces potentially serious or fatal arrythmias, or a benign ventricular disorder.

15. The method of claim 13, wherein the appropriate treatment is ventricle level shifting (VLS) therapy which uses premature ventricular contractions (PVC) blocking therapy, anti-tachycardia pacing (ATP) therapy, congestive heart failure (CHF) therapy which uses late systolic impulse (LSI) therapy, and cardiac resynchronization therapy (CRT) using a triangular electrical field that includes the shocking coil, or low voltage/medium voltage (LV/MV) therapy using arbitrary waveform therapy, to treat pulseless electrical activity (PEA) and/or asystole rescue.

16. The method of claim 13, wherein the benign ventricular disorder is irretractable ventricular bigeminy, trigeminy, or another idiopathic cause of excessive PVCs or VT or VF that effects the patient's well-being.

17. The method of claim 13, wherein VLS therapy comprises delivering a subthreshold, atraumatic, negative, tonic voltage stimulus to a left ventricle (LV) and/or coronary sinus (CS) from an amplifier A3 lead to deliver voltage stimulus between an amplifier A4 in the right ventricle (RV) of a patient's heart and to also deliver further negative voltage between a shocking coil amplifier A2 to create a triangular electrical field whereby PVCs can be dynamically blocked within the intraventricular septum at the heart's apex to block and prevent PVCs which cause VF during the vulnerable period during a T wave or vulnerable period as defined herein causing a steerable conduction block that prevents PVCs from conducting from the upper intraventricular septum outflow tracts that conduct downward to the apex which are the pathways for PVCs to induce VF in the case of Brugada Syndrome or any other PVC triggered episode of VF which leads to SCA.

18. The method of claim 13, wherein delivering the VLS therapy during an episode of ventricular fibrillation using amplifiers A1, A2, A3, and A4 closes the sodium channels throughout the entire syncytium of the ventricles using multiple negative wavefronts and/or negative pulses whether pulsed or stepped to effectively defibrillate the ventricles.

19. The system of claim 1, wherein a single implantable cardiac device is capable of treating and managing several distinct cardiac disorders selected from the group consisting of VT/VF arbitrary waveform defibrillation, PVCs, CRT, CHF, PEA, Brugada Syndrome, R on T Phenomenon, Long QT Syndrome, Chronic ventricular bigeminy, trigeminy, Bradycardia, and shockless defibrillation and/or ascending ramp, arbitrary, or BTE high voltage shocking waveforms.

20. An implantable cardioverter defibrillator (ICD) system for administering cardiac therapy to a patient, which comprises:
   a subcutaneous case capable of being positioned under a patient's skin and in communication with the patient's heart;

an arbitrary waveform control system located within the subcutaneous case, the arbitrary waveform control system comprising:
  a microcontroller or FPGA having a memory; and
  differentially driven phased array amplifiers comprising hot can amplifier A1 and amplifiers A2, A3, and A4; and
  a battery;
one or more sensors;
a bipolar pacing lead to be positioned in a right ventricle (RV) of the patient's heart and in functional communication with amplifier A4;
a right ventricular (RV) pacing and shocking coil/defibrillation lead in functional communication with amplifier A2; and
a left ventricular (LV) and/or coronary sinus (CS) pacing lead in functional communication with amplifier A3,
wherein the bipolar pacing lead, amplifier A4, the right ventricular (RV) pacing and shocking coil/defibrillation lead, amplifier A2, the left ventricular (LV) and/or coronary sinus (CS) pacing lead, and amplifier A3 form a triangular electrical field, and
wherein, based upon sensor data and demand criteria software programmed into the memory of the microcontroller or FPGA, the bipolar pacing lead, the right ventricular pacing and shocking coil/defibrillation lead, and the left ventricular and/or coronary sinus pacing lead deliver cardiac therapy to the patient's heart.

21. A method of treating a cardiac condition in a patient, which comprises implanting an implantable cardiac system of claim 20 into the patient and administering appropriate treatment to the patient.

\* \* \* \* \*